United States Patent [19]

Desmurs et al.

[11] Patent Number: 4,983,781

[45] Date of Patent: Jan. 8, 1991

[54] PROCESS FOR THE PREPARATION OF 4,4'-DIBROMOBIPHENYL IN A SOLVENT MEDIUM AND WITH A CATALYST

[75] Inventors: Jean-Roger Desmurs, Saint Symphorien D'Ozon; Alain Nonn, Sainte Foy Les Lyon, both of France

[73] Assignee: Rhone Poulenc Chimie, Courbevoie, France

[21] Appl. No.: 314,133

[22] Filed: Feb. 23, 1989

[30] Foreign Application Priority Data

Mar. 2, 1988 [FR] France ................................ 88 02608

[51] Int. Cl.$^5$ ........................ C07C 17/12; C07C 25/18
[52] U.S. Cl. ............................... 570/210; 570/206.000; 570/208.000
[58] Field of Search ......................... 570/208, 210, 206

[56] References Cited

FOREIGN PATENT DOCUMENTS 1142550  3/1983  Canada ................................. 570/210
2144259  3/1972  Fed. Rep. of Germany ...... 570/210
 913587 12/1962  United Kingdom ................ 570/210

*Primary Examiner*—Werren B. Lone
*Attorney, Agent, or Firm*—Finnegan, Henderson, Farabow, Garrett and Dunner

[57] ABSTRACT

The preparation of 4,4'-dibromobiphenyl. A biphenyl is reacted with bromine in a solvent in the presence of a catalytic system based on at least one component selected from the group consisting of Lewis acids and iodine.

14 Claims, No Drawings

PROCESS FOR THE PREPARATION OF 4,4'-DIBROMOBIPHENYL IN A SOLVENT MEDIUM AND WITH A CATALYST

The invention relates to the preparation of 4,4'dibromobiphenyl.

4,4'-Dibromobiphenyl is a compound which by hydrolysis gives access to 4,4'-dihydroxybiphenyl, the latter product being a monomer for thermotropic polymers in particular, or a substance which can be used as a stabilizing agent.

There are already a number of processes for the preparation of 4,4'-dibromobiphenyl. However, a need has made itself felt for an industrial process which permits the bromination reaction to be activated and which makes it possible at the same time to maintain the degree of selectivity with respect to 4,4'dibromobiphenyl at a high level.

The process according to the invention for the preparation of 4,4'-dibromobiphenyl is characterized by reacting the biphenyl with bromine in a solvent and in the presence of a catalytic system based on at least one component selected from the group consisting of Lewis acids and iodine.

Certain embodiments of the process of the invention make it possible to obtain yields of greater than 85% at ambient temperature.

The solvent is preferably selected from the group consisting of aliphatic, cyclic and aromatic hydrocarbon solvents and their halogenated equivalents and nitrated solvents. It is more preferable to use solvents which are inert with respect to bromine. It is possible to use nitrated solvents with advantage as they permit much shorter reaction times to be achieved. Exemplary solvents include carbon tetrachloride, dichloromethane, 1,2-dichloroethane, o-dichlorobenzene and nitrobenzene, which is a nitrated solvent.

The concentration of biphenyl in the starting medium preferably ranges from 0.1 to 3 moles/l. It is more preferably from 1 to 2 moles/l.

The catalytic system may be composed of at least one Lewis acid or iodine or a mixture of the two.

The Lewis acid used is preferably one comprising a cation of an element of any one of the groups IIb, IIIa, IVb, Va, Vb, VIa, and VIII of the periodic table. Mention may be made in this case of iron, zinc, antimony, tellurium, zirconium, titanium, aluminium, gallium, hafnium, niobium, phosphorus and boron.

More preferably, the Lewis acid cation is bonded to at least one halide, such as, for example, $FeCl_3$, $ZnCl_2$, $SbCl_5$, $PBr_3$, $AlCl_3$, $TiCl_4$ and $ZrCl_4$.

In accordance with another embodiment of the invention, it is possible to use a catalytic system based on at least one Lewis acid or iodine but also comprising a component selected from the group consisting of amines, phosphines and sulphides.

It should be noted that it would not be a departure from the scope of the invention to make use of a catalytic system based on iodine, at least one Lewis acid and/or components of the type mentioned in the previous paragraph.

With regard to amines, it is preferred to use tertiary amines.

With regard to phosphines, it is preferred to use alkyl phosphines, aryl phosphines such as triphenylphosphine and alkylaryl phosphines.

With regard to sulphides, mention may be made of dialkyl sulphides, diaryl sulphides such as diphenylsulphide and dialkylaryl sulphides.

It is preferred that the amount of catalyst range from 0.1 to 10 mole percent with respect to the biphenyl involved and more preferably from 0.5 to 2 mole percent.

In the case of a catalytic system based on at least one Lewis acid and another component, the molar ratio of component to Lewis acid depends on the nature of the component/Lewis acid pairing. The preferred ratio is close to 1 or equal to 1.

In the case of a catalytic system based on iodine and another component, the preferred molar ratio of component to iodine is also close to 1 or equal to 1.

The reaction is generally produced by pouring the bromine into a mixture comprising the biphenyl, the solvent and the catalytic system.

An excess of bromine of from 0 to 20% with respect to stoichiometry is usually employed.

The reaction is carried on at a temperature which in most cases preferably varies from 0° to 60° C. It is more preferable for operation to be at ambient temperature.

The following examples further illustrate preferred embodiments of the present invention. The examples should in no way be considered limiting, but are merely illustrative of the various features of the present invention.

EXAMPLE 1

The following are introduced into a 250 ml reactor provided with a mechanical agitator, a cooler, a pouring funnel and a thermometer:

15.4 g of biphenyl (0.1 mole),
100 ml of solvent,
the amount of iodine indicated in Table 1 below.

The bromine (35.2 g–0.22 mole) is poured in at ambient temperature over a period of 10 minutes and then the medium is agitated for a variable period of time at ambient temperature. At the end of the reaction the excess of bromine and the iodine are destroyed by sodium sulphite or bisulphite.

The organic phase is washed, dried and diluted to a given volume to be analyzed with respect to CPG.

The other operating conditions and the results are set out in Table 1 below.

TABLE 1

| TEST | SOLVENT | CATALYST | DURATION | TRANSFORMATION RATE % | YIELD 4-Br (a) | 2,4'-diBr (b) | 4,4'-diBr |
|---|---|---|---|---|---|---|---|
| 1A | $(CH_2Cl)_2$ | — | 48 H | 100 | 23 | 1 | 46.7 |
| 1B | $(CH_2Cl)_2$ | —$I_2$(1%) | 30 H | 100 | 2.3 | 2.5 | 65.0 |
| 1C | $CH_2Cl_2$ | — | 29 H | 99 | 42 | 1 | 23.6 |
| 1D | $CH_2Cl_2$ | —$I_2$(1%) | 27 H | 100 | 0 | 2.6 | 64.8 |
| 1E | $PhNO_2$ | —$I_2$(1%) | 3 H | 100 | 8.2 | 2.5 | 86.2 |

(a) This column reveals the yield of monobrominated derivative (b) This column reveals the yield of dibrominated derivative but in positions 2 and 4.

A review of Table 1 clearly shows the attraction of a catalytic system of the iodine type with regard to the level of reactivity (yield of 4,4'-diBr).

EXAMPLE 2

The same mode of operation as in Example 1 is used, but Lewis acids are employed as the catalyst.

The operating conditions and the results are set out in Table 2 below.

TABLE 2

| TEST | SOLVENT | CATALYST | DURATION | TRANSFORMATION RATE % | YIELD 4-Br (a) | YIELD 2,4'-diBr (b) | 4,4'-diBr |
|---|---|---|---|---|---|---|---|
| 2A | $CH_2Cl_2$ | $FeCl_3$ (10%) | 24 H | 100 | 0 | 16.7 | 50.4 + tri |
| 2B | $CH_2Cl_2$ | $FeCl_3$ (1%) | 3 H | 100 | 0 | 14.0 | 49.0 |
| 2C | $CH_2Cl_2$ | $ZnCl_2$ (1%) | 29 H | 100 | 17.0 | 1.7 | 50.3 |
| 2D | $CH_2Cl_2$ | $SbCl_5$ (1%) | 24 H | 100 | 9.6 | 2.3 | 56.7 |
| 2E | $CH_2Cl_2$ | $PBr_3$ (1%) | 26 H | 100 | 27.0 | 2.1 | 43.6 |

The use of a Lewis acid increases the level of reactivity as can be seen from Table 2.

EXAMPLE 3

The same mode of operation as above is also used, but a Lewis acid-iodine system is employed as the catalyst.

The other conditions and the results obtained are set out in Table 3 below.

TABLE 3

| TEST | SOLVENT | CATALYST | DURATION | TRANSFORMATION RATE % | YIELD 4-Br (a) | YIELD 2,4'-diBr (b) | 4,4'-diBr |
|---|---|---|---|---|---|---|---|
| 3A | $CH_2Cl_2$ | $I_2$(1%) $FeCl_3$ (1%) | 6 H | 100 | 3.3 | 3.4 | 87.4 |

EXAMPLE 4

The following are introduced into a 250 ml four-neck flask provided with a water cooler surmounted by an outlet towards a sodium hydroxide trap for destroying the hydrobromic acid formed, a dropping funnel, a mechanical agitator system and a thermometer:

30.8 g of biphenyl,
100 ml of dichloromethane,
0.32 g of ferric chloride,
0.05 g of iodine.

67.8 g of bromine are added dropwise while the reaction medium is maintained at ambient temperature by controlling the flow rate. The medium is kept at ambient temperature for 5 hours and then heated under reflux of dichloromethane for 1 hour. After the medium has returned to ambient temperature, the excess of bromine and the iodine are destroyed by a 10% sodium sulphite solution.

4,4'-Dibromobiphenyl, being weakly soluble in dichloromethane, can be filtered and washed with that solvent.

The residual solution is washed with water until neutral and then dried over sodium sulphate.

The yields with respect to the crude product obtained by CPG determination of the organic phase (mixture of crystals solution) are as follows:

Yields
(4,4'-diBr)=93.3%
(2,4'-diBr)=3.5%
(4-Br)=0.9%

Examples 3 and 4 show that the iodine-Lewis acid combination, besides an improved yield, gives a high level of selectivity (4,4'-diBr/2,4'-diBr ratio).

Additional advantages and modifications will readily occur to those skilled in the art. The invention in its broader aspects is, therefore, not limited to the specific details, representative apparatus and illustrative examples shown and described. Accordingly, departures may be made from such details without departing from the spirit or scope of the general inventive concept as defined by the appended claims and their equivalents.

What is claimed:

1. A process for the preparation of 4,4'-dibromobiphenyl comprising the step of reacting biphenyl with bromine in a solvent and in the presence a catalytic system based on at least one component selected from the group consisting of Lewis acids and iodine.

2. A process according to claim 1, wherein the solvent is selected from the group consisting of aliphatic, cyclic and aromatic hydrocarbon solvents and nitrated solvents.

3. A process according to claim 2, wherein said aliphatic, cyclic and aromatic hydrocarbon solvents are halogenated.

4. A process according to claim 1, wherein the Lewis acids contain a cation of an element of any one of the groups IIb, IIIa, IVb, Va, Vb, VIa and VIII of the periodic table.

5. A process according to claim 4, wherein said cation of said Lewis acid is bonded to at least one halide.

6. A process according to claim 1, wherein said catalytic system comprises at least one Lewis acid and a component selected from the group consisting of amines, phosphines and sulphides.

7. A process according to claim 1, wherein said catalytic system comprises iodine and at least one component selected from the group consisting of Lewis acids, amines, phosphines and sulphides.

8. A process according to claim 1, wherein said catalytic system is based on a Lewis acid and another component selected from the group consisting of iodine, amines, phosphines and sulfides and the ratio by weight of the component to the Lewis acid is close to 1 or equal to 1.

9. A process according to claim 1, wherein the amount of catalyst in the catalytic system ranges from 0.1 to 10 mole percent, with respect to the biphenyl.

10. A process according to claim 8, wherein the amount of catalyst in the catalytic system ranges from 0.5 to 2 mole percent, with respect to the biphenyl.

11. A process according to claim 1, wherein the reaction is carried out at a temperature from 0° to 60° C.

12. A process according to claim 1, wherein the solvent is a nitrated solvent.

13. A process according to claim 12, wherein the nitrated solvent is nitrobenzene.

14. A process for the preparation of 4,4'-dibromobiphenyl comprising the step of reacting biphenyl with bromine in a solvent and in the presence of a catalytic system based on at least one component selected from the group consisting of Lewis acids and iodine wherein an excess of bromine of from about 0 to 20% with respect to stoichiometry is employed.

* * * * *

UNITED STATES PATENT AND TRADEMARK OFFICE
CERTIFICATE OF CORRECTION

PATENT NO. :   4,983,781

DATED      :   January 8, 1991

INVENTOR(S) :  Jean-Roger Desmurs et al.

It is certified that error appears in the above-identified patent and that said Letters Patent is hereby corrected as shown below:

Claim 1, col. 4, line 46, after "presence" insert --of--.

Signed and Sealed this

Twenty-second Day of September, 1992

Attest:

DOUGLAS B. COMER

*Attesting Officer*        *Acting Commissioner of Patents and Trademarks*